(12) United States Patent
Lee

(10) Patent No.: US 10,695,088 B2
(45) Date of Patent: Jun. 30, 2020

(54) LIFTING SURGICAL INSTRUMENT HAVING BRANCH POINT

(71) Applicant: Jun-Sung Lee, Seoul (KR)

(72) Inventor: Jun-Sung Lee, Seoul (KR)

(*) Notice: Subject to any disclaimer, the term of this patent is extended or adjusted under 35 U.S.C. 154(b) by 211 days.

(21) Appl. No.: 15/702,598

(22) Filed: Sep. 12, 2017

(65) Prior Publication Data

US 2018/0098787 A1    Apr. 12, 2018

(30) Foreign Application Priority Data

Oct. 6, 2016    (KR) .................. 10-2016-0129081

(51) Int. Cl.
*A61B 17/34*    (2006.01)
*A61B 90/00*    (2016.01)
(Continued)

(52) U.S. Cl.
CPC ...... *A61B 17/3417* (2013.01); *A61B 17/0482* (2013.01); *A61B 17/06109* (2013.01); *A61B 17/3415* (2013.01); *A61B 17/3468* (2013.01); *A61B 17/3478* (2013.01); *A61B 90/02* (2016.02); *A61B 17/06166* (2013.01); *A61B 2017/00455* (2013.01); *A61B 2017/00477* (2013.01); *A61B 2017/00747* (2013.01); *A61B 2017/00792* (2013.01);
(Continued)

(58) Field of Classification Search
CPC ............ A61B 17/3421; A61B 17/3417; A61B 17/3468; A61B 17/3494; A61B 17/3496; A61B 17/06; A61B 17/0482; A61B 17/06066; A61B 2017/3454; A61B 2017/348; A61B 2017/3492; A61M 25/06; A61M 25/0612
See application file for complete search history.

(56) References Cited

U.S. PATENT DOCUMENTS

| | | | | |
|---|---|---|---|---|
| 5,954,670 A | * | 9/1999 | Baker ................ | A61B 17/3403 600/567 |
| 6,203,524 B1 | * | 3/2001 | Burney .............. | A61B 10/0233 128/898 |

(Continued)

FOREIGN PATENT DOCUMENTS

| | | |
|---|---|---|
| CN | 202235596 U | 5/2012 |
| JP | 2006-288615 A | 10/2006 |

(Continued)

*Primary Examiner* — Ashley L Fishback
(74) *Attorney, Agent, or Firm* — KORUS Patent, LLC; Seong Il Jeong

(57) ABSTRACT

Disclosed herein is a lifting surgical instrument having a branch point, which is used to insert a thread without a cog and a barb into the skin. The lifting surgical instrument includes a sheath, including: a probe part formed in the tubular shape in which a through hole penetrating in a longitudinal direction is formed, and configured such that the front end thereof may be inserted into the skin; and a body configured to extend from the rear end of the probe part, to have a diameter larger than that of the through hole, to communicate with the through hole, and to include a sheath hole. In this case, a direction guidance portion is provided on the inner surface of the probe part, and the angle at which the needle travels is changed via the direction guidance portion when the needle passes through the through hole.

7 Claims, 13 Drawing Sheets

(51) Int. Cl.
*A61B 17/04* (2006.01)
*A61B 17/06* (2006.01)
*A61B 17/00* (2006.01)
*A61M 25/01* (2006.01)
*A61M 25/00* (2006.01)

(52) U.S. Cl.
CPC ........... *A61B 2017/06019* (2013.01); *A61B 2017/06052* (2013.01); *A61B 2017/06176* (2013.01); *A61B 2017/3409* (2013.01); *A61B 2017/3454* (2013.01); *A61B 2090/036* (2016.02); *A61M 25/0102* (2013.01); *A61M 2025/009* (2013.01); *A61M 2025/018* (2013.01)

(56) References Cited

U.S. PATENT DOCUMENTS

| | | | | |
|---|---|---|---|---|
| 2006/0036158 A1* | 2/2006 | Field | ............ | A61B 90/39 600/414 |
| 2012/0199060 A1* | 8/2012 | Furbush, Jr. | ............ | A61B 5/065 116/201 |

FOREIGN PATENT DOCUMENTS

| | | |
|---|---|---|
| JP | 2010-075318 A | 4/2010 |
| KR | 20-2008-0004109 U | 9/2008 |
| KR | 10-1502074 B1 | 3/2015 |
| KR | 10-1682419 B1 | 12/2016 |

\* cited by examiner

LIFTING SURGICAL INSTRUMENT HAVING BRANCH POINT

BACKGROUND

1. Technical Field

The present invention relates to a lifting surgical instrument which is used to lift a tissue by moving a tissue layer under a skin layer in an upward direction or which is used to insert a thread into the skin in order to remove a wrinkle by moving a lower skin layer in an upward direction. More specifically, the present invention relates to a lifting surgical instrument having a branch point, which uses a sheath as a branch point in order to form a thread without a cog and a barb in a ring shape under the skin and to perform a lifting surgery.

2. Description of the Related Art

Generally, a plastic surgery is a generic term for surgical operations which are performed chiefly for the correction of a partially damaged or deformed part of a human body or for cosmetic treatment. Recently, surgical operations for cosmetic treatment have become commonplace. Among the surgical operations for cosmetic treatment, a surgical operation for anti-aging has been attracting attention. In particular, a face lifting operation has been attracting increasing attention.

As a person ages, in other words, as an aging process proceeds over time, the skin and various layers under the skin droop downward due to gravity, and thus the appearance of a face becomes aged. Basically, there are two types of surgical methods which are performed in order to alter this aged appearance so as to provide a more youthful appearance. One is an invasive method in which a relatively long incision is made in the skin, and the other is a minimally invasive method which uses a thread.

In the invasive method in which an incision is made, a long incision is directly made in the skin, a skin layer is dissected, a thread is directly inserted into a droopy subcutaneous tissue under direct vision (i.e., while the droopy subcutaneous tissue is being directly observed), and then the droopy subcutaneous tissue is lifted. The invasive method provides a desirable effect, but is disadvantageous in that the time required to perform the invasive method is relatively long, bleeding occurs during the process of directly making an incision, and surgical scars may be left.

The minimally invasive method has been proposed to mitigate the above disadvantages. In the minimally invasive method, a thread with cogs or barbs is inserted under a skin layer, and a droopy subcutaneous tissue is lifted by using force attributable to the cogs or barbs. The minimally invasive method is advantageous in that the time required to perform the minimally invasive method is shorter than that required to perform the invasive method, surgical scars are small, and the amount of bleeding is small.

Conventional lifting surgical instruments used to perform the minimally invasive method will be described with reference to FIGS. 1 and 2. One of the conventional lifting surgical instruments includes a sheath 10, a needle 20 connected to a thread 30, and the thread 30. More specifically, referring to FIG. 1, the sheath 10, in which the front end thereof has an inclined surface and a through hole penetrates therethrough in a longitudinal direction, is inserted into the skin, the thread 30 is passed through the through hole of the sheath 10, and the thread 30 is moved to the front end of the sheath 10. Thereafter, when the sheath 10 is removed, the thread 30 is left in a subcutaneous tissue.

The thread 30 includes cogs or barbs, the cogs or barbs have directionality, and the cogs or barbs provide fastening force in a direction opposite to the direction, in which the thread 30 has been inserted, when the thread 30 has been inserted into a subcutaneous tissue. Accordingly, when the thread 30 left in the subcutaneous tissue is pulled, the cogs or barbs are caught in the subcutaneous tissue, the droopy tissue is lifted by the fastening force generated by the cogs or barbs, and thus a wrinkle may be removed.

Furthermore, as shown in FIG. 2, a lifting surgery may be performed based on a principle identical to that of the above case by directly passing the needle 20 connected to the thread 30 through the skin without using the sheath 10 and inserting the thread 30 into a subcutaneous tissue.

This conventional technology may cause problems as follows:

First, the cogs or barbs of the thread 30 are formed on the sides of the thread 30, have directionality, and are formed in a wing shape through partial cutting. Accordingly, sufficient fastening force may not be provided via the cogs or barbs due to the thinness of the thread 30. The fastening force may be increased by increasing the thickness of the thread 30. When the thread 30 is thick, a patient may have the sensation of a foreign substance upon insertion into a skin tissue, thereby causing the patient discomfort. Although the fastening force may be increased by inserting a plurality of threads 30 into the skin, a plurality of insertion holes is thus required. Accordingly, a number of scars are left after a lifting surgery, thereby causing an aesthetic problem. Furthermore, as the number of threads 30 increases, the conventional technology becomes more problematic in that the sensation of a foreign substance attributable to the threads 30 may occur, the threads 30 may protrude, and inflammation may be caused by the threads 30.

Second, the cogs or barbs of the thread 30 are disposed not only in the droopy subcutaneous tissue which a surgeon desires to lift, but also in another subcutaneous tissue, thereby causing a problem in that an unintentional lifting of another subcutaneous tissue may occur.

Third, the cogs or barbs may be damaged or lost when the thread 30 is linearly pulled. Accordingly, the skin and a subcutaneous tissue are unevenly lifted, thereby causing an effect different from an expected effect. Furthermore, due to the phenomenon of the traction of the periphery of a surgical site occurring after a surgery, the cogs or barbs may be damaged or lost when a patient moves a facial muscle, thereby causing a problem in that sufficient fastening force may not be provided.

Fourth, the ends of the cogs or barbs are sharp due to the structure of the cogs or barbs on the thread 30, and thus a tissue may be damaged or a patient may suffer from pain.

PRIOR ART DOCUMENT

Patent Document (Patent document 1) Korean Patent Application Publication No. 10-2014-0092096 (published on Jul. 23, 2014)

SUMMARY

The present invention has been conceived to overcome the above-described problems, and an object of the present invention is to provide a lifting surgical instrument having a branch point, which uses a sheath as a branch point in order to form a thread without a cog and a barb in a ring shape under the skin and to perform a lifting surgery.

In order to achieve the above-described object, according to the present invention, there is provided a lifting surgical instrument having a branch point, the lifting surgical instrument including a sheath, wherein the sheath includes: a probe part formed in the tubular shape in which a through hole penetrating in a longitudinal direction is formed, and configured such that the front end thereof may be inserted into the skin; and a body configured to extend from the rear end of the probe part, to have a diameter larger than that of the through hole of the probe part, to communicate with the inside of the through hole, and to include the sheath hole into which a needle may be inserted. In this case, a direction guidance portion configured to protrude from the inner surface of the probe part to the through hole is provided on the inner surface of the probe part, and the angle at which the needle travels is changed via the direction guidance portion when the needle passes through the through hole of the probe part.

The lifting surgical instrument having a branch point according to the present invention may further include an indicator configured to extend the outer diameter of the probe part when the indicator is inserted over the outer surface of the probe part, to slide in the longitudinal direction of the probe part, and to be fastened to the probe part at a predetermined location, thereby being caught by an introduction hole in the skin so that the probe part can be located at a desired location under the skin when the probe part is inserted into the skin.

The direction guidance portion of the lifting surgical instrument having a branch point according to the present invention may be provided at the front end of the probe part. The direction guidance portion may form a rising curve on the inner surface of the probe part, and may extend to one end of the probe part. The direction guidance portion of the lifting surgical instrument having a branch point according to the present invention may be formed to have a semicircular or semielliptical sectional shape.

The indicator of the lifting surgical instrument having a branch point according to the present invention may include: an indicator body configured to include the insertion hole which penetrates the inner and outer surfaces thereof; and a location fastening member configured to be inserted into the insertion hole so that the indicator can be fastened to the probe part at the predetermined location. In this case, screw grooves may be formed in the inner surface of the insertion hole formed in the indicator body, the location fastening member may include a bolt and be screwed into the insertion hole, and the indicator may be fastened to the probe part at the predetermined location when one end of the bolt inserted into the insertion hole comes in contact with the outer surface of the probe part.

The indicator of the lifting surgical instrument having a branch point according to the present invention may include a body part and a cover part configured to be inserted over the body part. In this case, the body part may include a cylindrical base part and a screw part configured to extend from the base part and to include bolt threads, and screw grooves may be formed in the inner surface of the cover part. The cover part may be inserted over the screw part through screw coupling, and the diameter of the inner surface of the cover part in which the screw grooves are formed may be smaller than that of the screw part. The screw part may be tightened when the cover part is inserted over the screw part and coupled to the screw part. A marking point may be provided on the outer surface of the body part or cover part.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
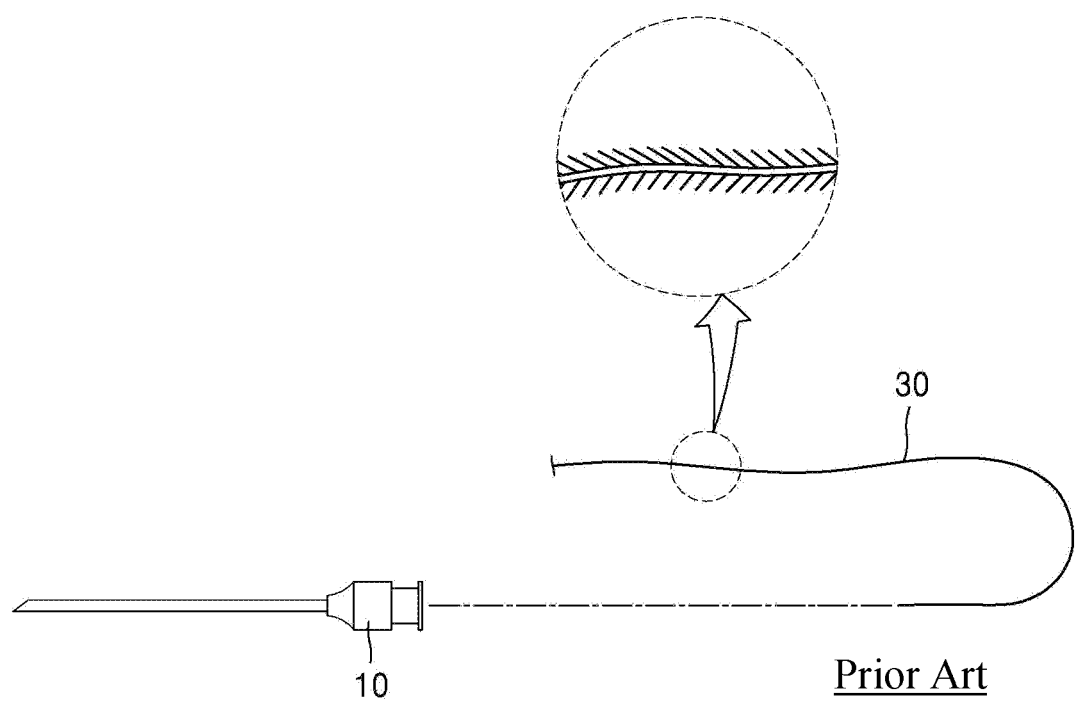
FIG. 1 is a view showing an assembled lifting surgical instrument according to an embodiment of a conventional technology.
Figure 2:
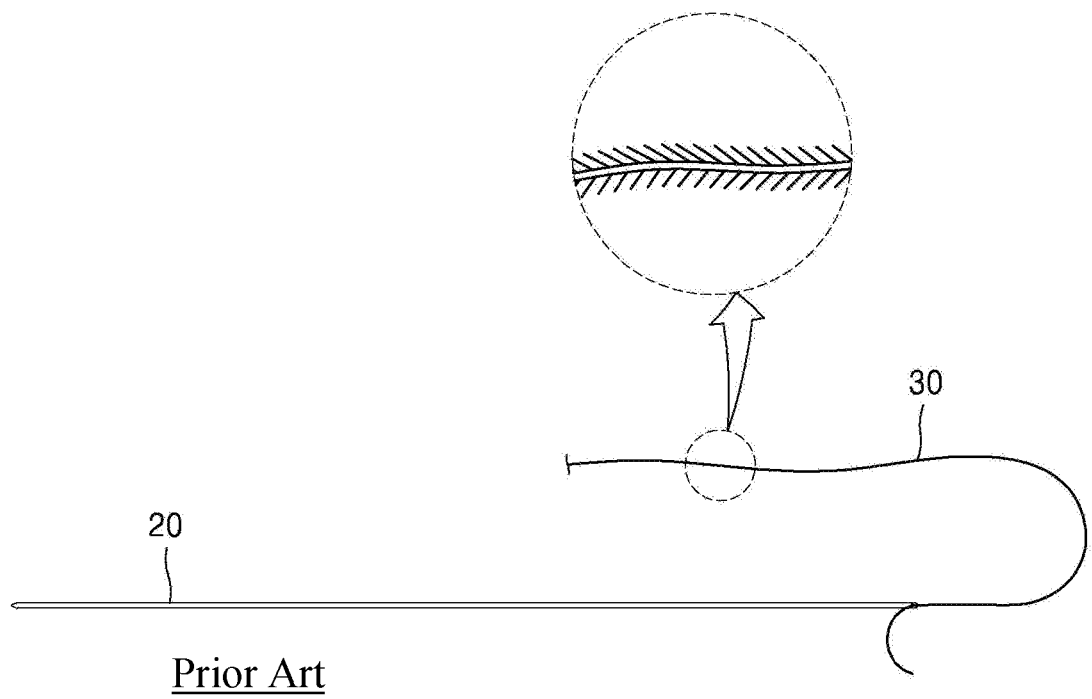
FIG. 2 is a view showing another assembled lifting surgical instrument according to another embodiment of the conventional technology.

A lifting surgical instrument 100 according to the present invention is used to form a thread 131 without a cog and a barb in a ring shape under the skin and to perform a lifting surgery. The lifting surgical instrument 100 relates to a lifting surgical instrument having a branch point, which enables the front end of a sheath 110 to be disposed at a desired location in a subcutaneous tissue by using an indicator 120 and uses the sheath 110 as a branch point so that a thread 131 without a cog and a barb can be formed in a ring shape under the skin.

The lifting surgical instrument 100 according to the present invention is a surgical instrument for a surgical method which has been newly conceived by the applicant of the present invention. The newly conceived surgical method is configured to form the thread 131 without a cog and a barb in a ring shape at a desired location within the tissue and to lift a droopy tissue, unlike the conventional lifting surgical methods configured to insert a thread with cogs or barbs into a subcutaneous tissue and to pull the thread.

A needle is required to pass through a sheath twice in order to form a thread in a ring shape at a desired location within a tissue. Meanwhile, a ring shape may not be formed at a desired location by simply passing a needle through a sheath twice because the traveling path of the needle within a subcutaneous tissue formed after passing through the sheath for the first time may overlap the traveling path of the needle within the subcutaneous tissue formed after passing through the sheath for the second time. Accordingly, the traveling paths of a needle are required to branch off from each other at a desired location in order to form a thread in a ring shape at a desired location. In order to form an accurate branch point for a needle, the lifting surgical instrument 100 according to the present invention includes a bump (i.e., a direction guidance portion 150) formed on the inner surface of the probe part 111 of the sheath 110, and changes the angle of the direction in which the needle travels via the bump when the needle passes through the sheath 110.

The lifting surgical instrument 100 according to the present invention includes the sheath 110 including the probe part 111 and a body 112, an indicator 120, and the direction guidance portion 150. A preferred embodiment of the present invention will be described in detail with reference to the accompanying drawings below.

Figure 9:
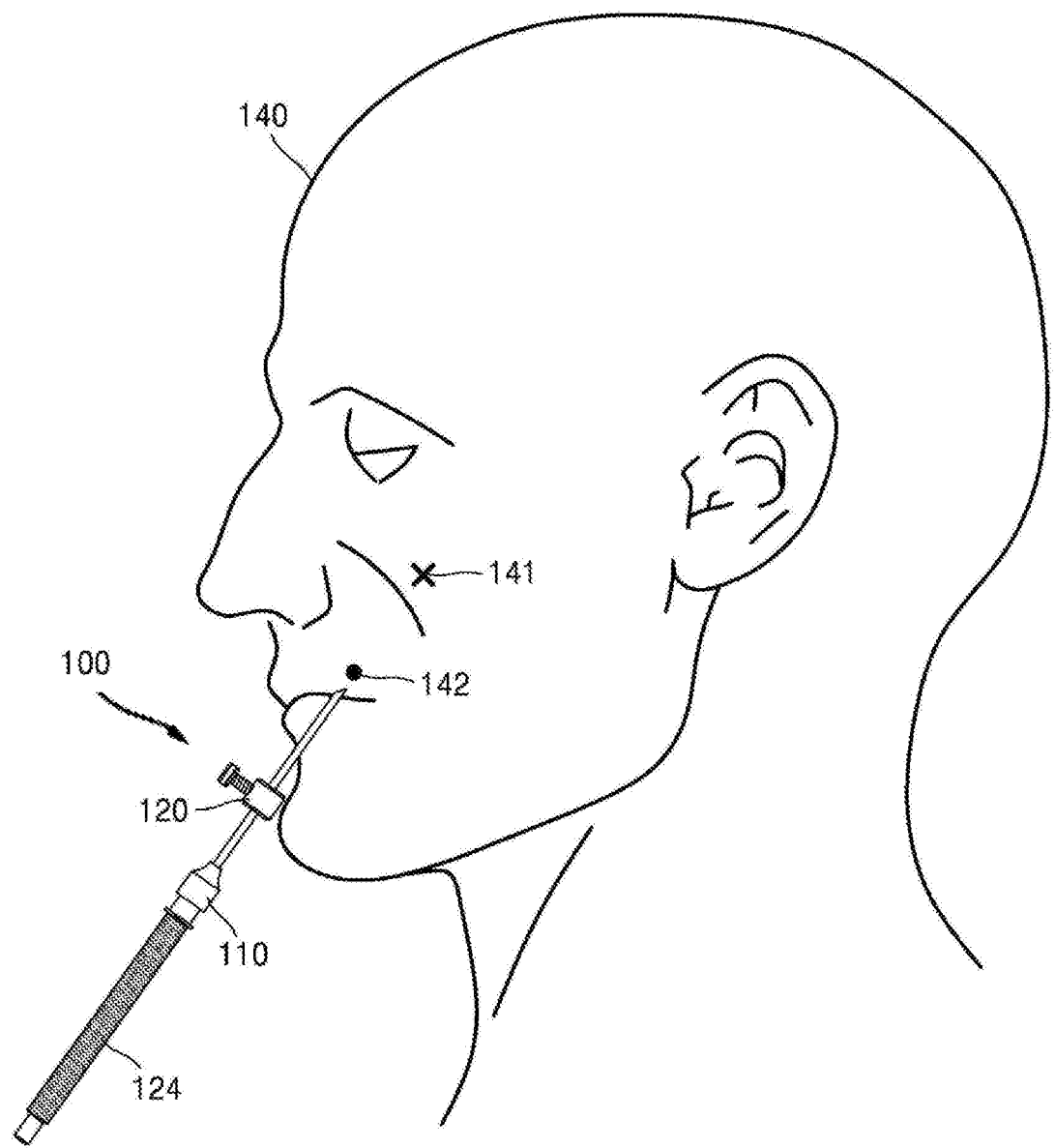
FIGS. 9 to 13 are views showing a surgical method using a thread without a cog and a barb and a lifting surgical instrument having a branch point according to the present invention.
Figure 10:
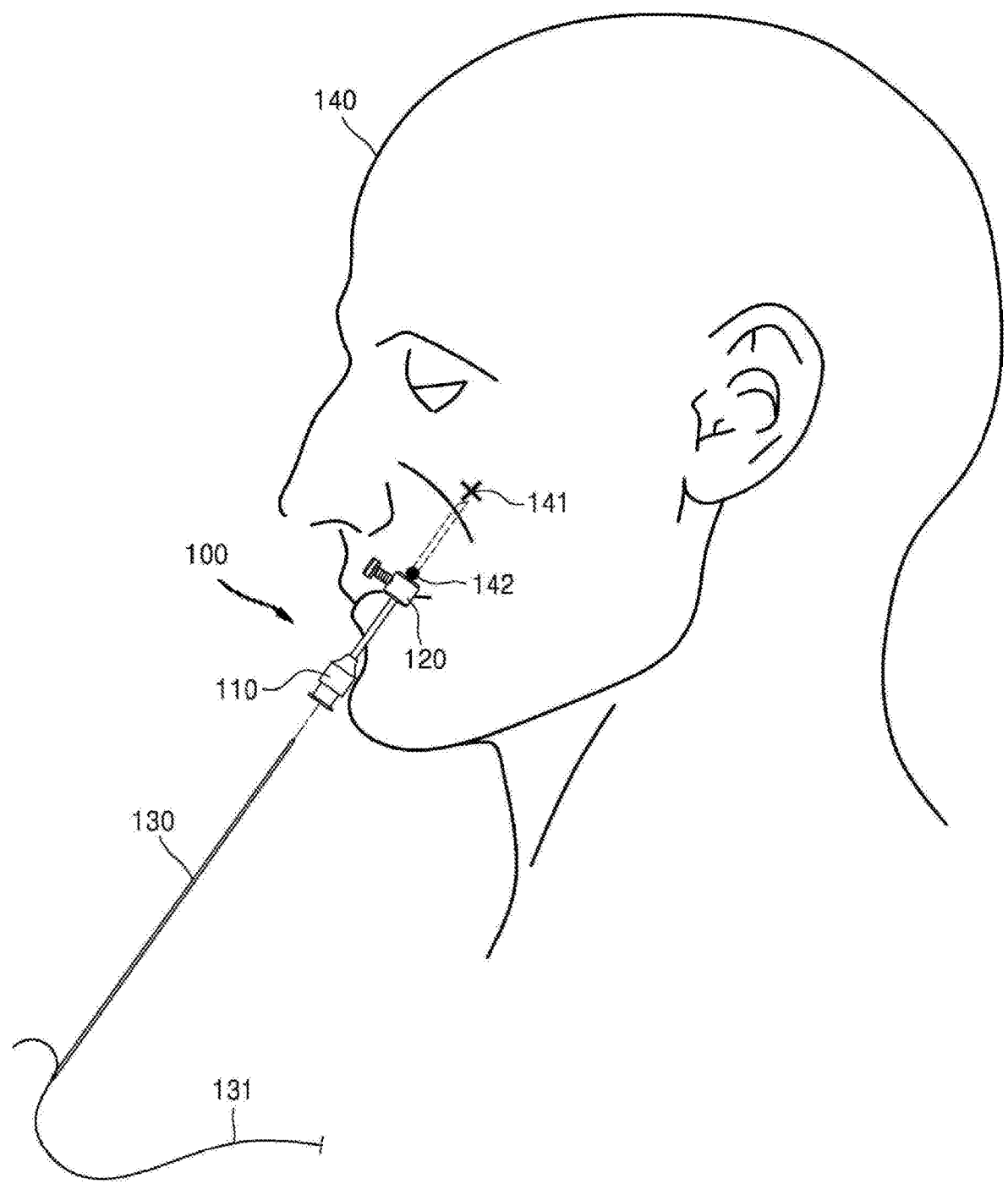

The entire lifting surgical instrument 100 of the present invention is shown, for example, in FIG. 9, and FIG. 10 shows the lifting surgical instrument 100 from which some components are removed in order to explain functions of the needle 130.

Figure 3:
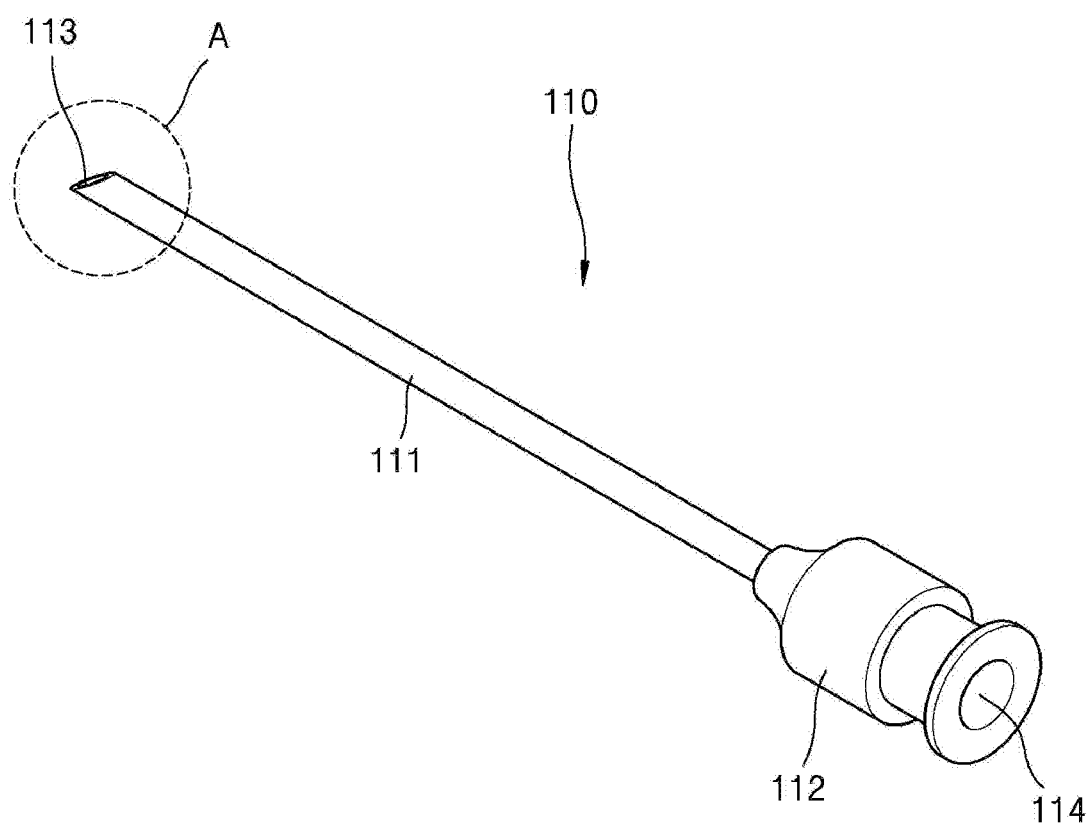
FIG. 3 is a perspective view showing a sheath according to an embodiment of the present invention.

Referring to FIG. 3, the sheath 110 includes the probe part 111 and the body 112. The probe part 111 is formed in a tubular shape in which a through hole 113 configured to penetrate the probe part 111 in a longitudinal direction is formed, and the front end of the probe part 111 has an inclined surface. A portion of the probe part 111 may be inserted into the skin through an introduction hole 142 after the introduction hole 142 has been formed in the surface of the skin via an injection needle or needle. The sectional shape of the front end of the probe part 111 forms an inclined cross section. When the probe part 111 has been inserted into the skin, a needle 130 to which a thread has been coupled passes through the through hole 113 which penetrates the inside of the probe part 111.

The body 112 is connected to the rear end of the probe part 111, and is expanded. The body 112 includes a sheath hole 114 configured to communicate with the through hole 113 disposed inside the probe part 111, and the diameter of the sheath hole 114 is larger than that of the through hole 113. The needle 130 is inserted through the sheath hole 114. The needle 130 is easily inserted because the sheath hole 114 has a larger diameter than the through hole 113. The inserted needle 130 is moved forward through the through hole 113 which communicates with the sheath hole 114.

The direction guidance portion 150 configured to protrude from the inner surface of the probe part 111 into the through hole 113 is provided on the inner surface of the probe part 111.

Figure 4A:
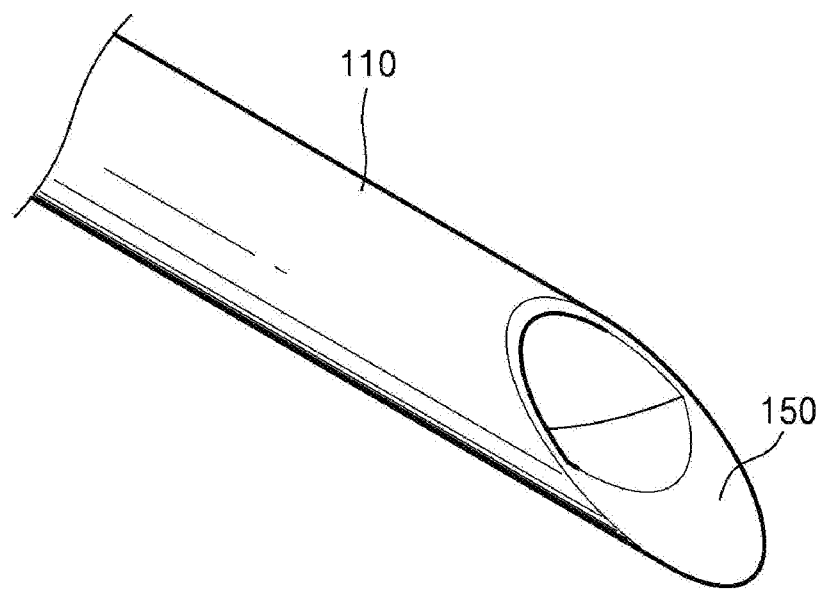
FIGS. 4a and 4b are enlarged views of the probe part (i.e., portion A) shown in FIG. 3.
Figure 4B:
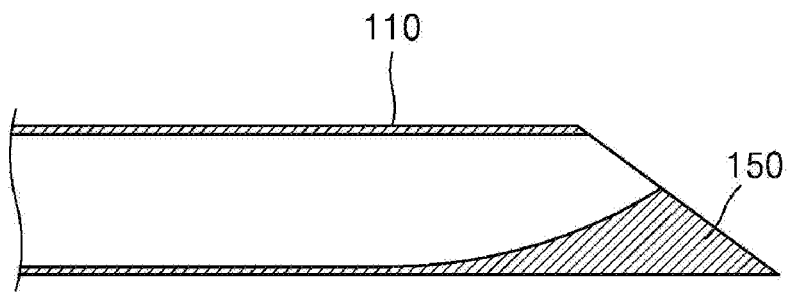

The direction guidance portion 150 changes the angle at which the needle 130 travels when the needle 130 passes through the through hole 113 of the probe part 111, thereby changing the path of the needle 130. Referring to FIGS. 4a and 4b, the direction guidance portion 150 may be provided at the front end of the probe part 111, the direction in which the needle 130 travels is changed at the front end of the probe part 111 via the direction guidance portion 150, and then the needle 130 passes through the probe part 111. The location of the direction guidance portion 150 is not limited thereto, but the direction guidance portion 150 may be formed at any one of various locations. For example, the direction guidance portion 150 may be provided in the middle portion of the probe part 111, in which case the direction in which the needle 130 travels may be changed in the middle portion of the probe part 111.

Referring to FIG. 4b, the direction guidance portion 150 may form a rising curve on the inner surface of the probe part 111, and may extend to one end of the probe part 111. The direction guidance portion 150 forms the rising curve, and thus the direction in which the needle 130 travels may be gradually changed along the rising curve. It will be apparent that the shape of the direction guidance portion 150 is not limited thereto but the direction guidance portion 150 may be formed in any one of various shapes as long as these shapes change the direction in which the needle 130 travels.

Figure 5:
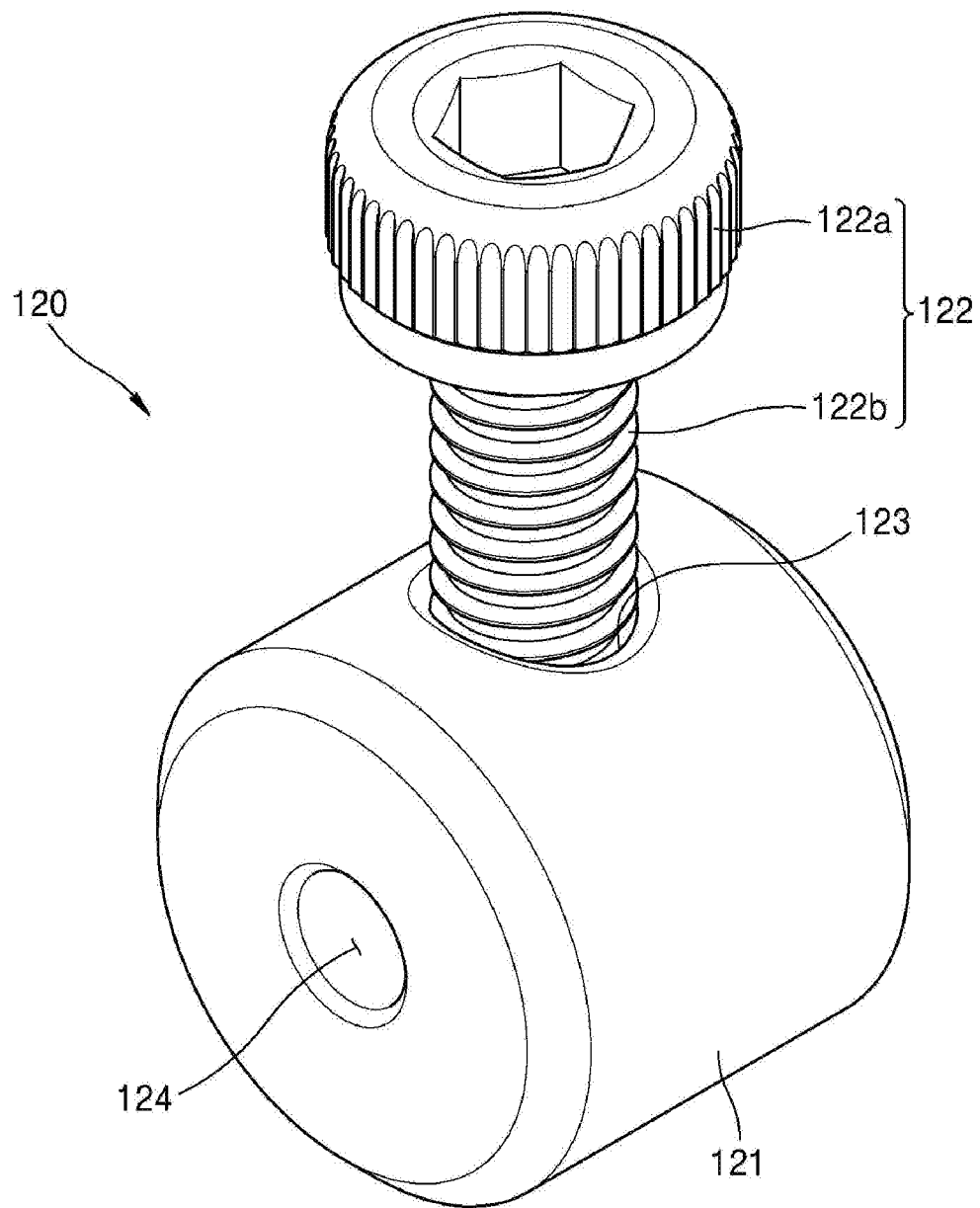
FIG. 5 is a perspective view showing an indicator according to an embodiment of the present invention.

Referring to FIG. 5, the indicator 120 is inserted over the outer surface of the probe part 111, and extends the outer diameter of the probe part 111. The indicator 120 may slide in the longitudinal direction of the probe part 111, and may be fastened by tightening a location fastening member at a predetermined location on the probe part 111. The predetermined location which is present on the probe part 111 and at which the indicator 120 is fastened is determined based on the location at which the front end of the probe part 111 is located within a subcutaneous tissue and the location of the introduction hole 142 through which the probe part 111 is inserted. The location (i.e., a lifting location 141) at which the front end of the probe part 111 is located is the location at which a surgeon intends to lift a droopy tissue or a subcutaneous tissue around a wrinkle. The outer diameter of the portion of the probe part 111 on which the indicator 120 has been disposed is extended at the predetermined location. Accordingly, when the probe part 111 is inserted into the skin, only the portion of the probe part 111 before the indicator 120 is inserted, and the indicator 120 is caught by the introduction hole 142.

The indicator 120 may include the indicator body 121 and the location fastening member. The indicator body 121 is formed in a cylindrical shape, and has an upper surface, a lower surface, and an outer surface. A body hole configured to penetrate the center of the upper surface and the center of the lower surface is formed in the indicator body 121, and the indicator body 121 includes an insertion hole 123 configured to penetrate the outer surface of the indicator body 121 and the inner surface of the indicator body 121 (i.e., the inner surface of the body hole). The location fastening member is inserted into the insertion hole 123, and fastens the indicator 120 to the probe part 111 at a predetermined location.

More specifically, bolt threads are formed on the inner surface of the insertion hole 123 configured to penetrate the outer surface of the indicator body 121 and the inner surface of the indicator body 121 (i.e., the inner surface of the body hole 124), and the location fastening member is composed of a bolt 122. Accordingly, the bolt 122 is inserted into the indicator body 121 through screw coupling (in other words, the indicator body 121 functions as a nut).

Figure 6:
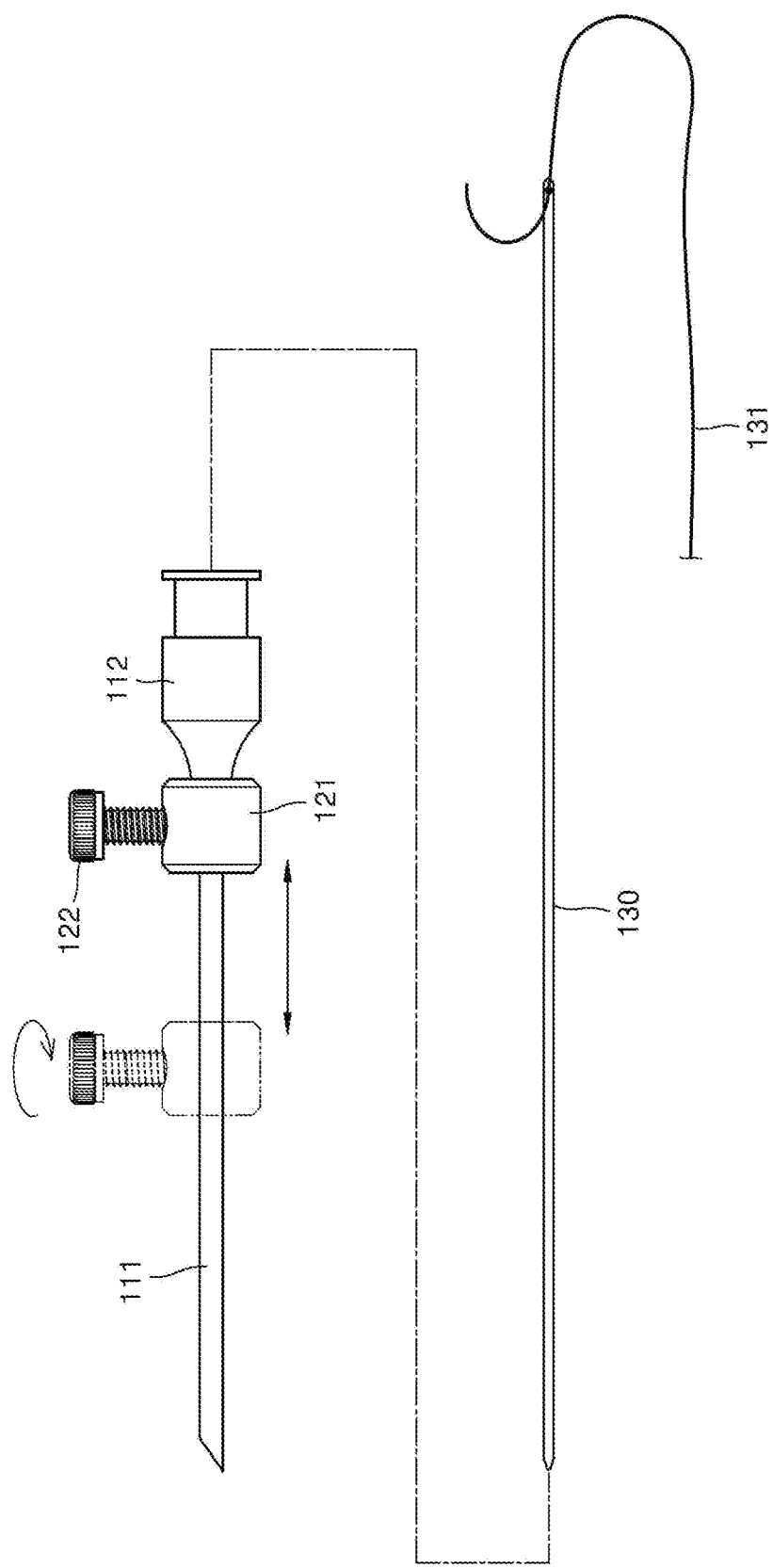
FIG. 6 is a view showing the operations of a sheath shown in FIG. 3 and an indicator shown in FIG. 5.

Referring to FIG. 6, when the indicator 120 is slid in the longitudinal direction of the probe part 111 and then fastened at a predetermined location, the bolt 122, which is a location fastening member, is screwed into the insertion hole 123. In this case, the bolt 122, which is a location fastening member, is sufficiently tightened such that one end of the bolt 122 comes in contact with the outer surface of the probe part 111 inserted into the body hole. When the one end of the bolt 122 comes in contact with the outer surface of the probe part 111, frictional force is generated, and thus the indicator 120 is fastened and prevented from sliding.

The bolt 122 includes the bolt thread portion 122b configured such that bolt threads are formed thereon, and a bolt head 122a configured to be disposed on the bolt thread portion 122b and to have an increased outer diameter. Grooves are formed in the outer surface of the bolt head 122a in a circumferential direction at predetermined intervals, and the grooves prevent the bolt 122 from slipping when a surgeon tightens the bolt 122.

Figure 7:
FIG. 7 is a perspective view showing a stylet according to an embodiment of the present invention.

Referring to FIG. 7, the reference numeral "124" designates a stylet 124. The stylet 124 is inserted into the through hole 113 of the probe part 111, and is inserted into the skin along with the probe part 111 when the probe part 111 is inserted into the skin, thereby preventing the through hole 113 from being filled with a subcutaneous tissue. The diameter of the stylet 124 is slightly smaller than the inner diameter of the probe part 111 so that the stylet 124 is inserted into the through hole 113 inside the probe part 111, and the stylet 124 is formed in a bar shape. Since the probe part 111 is formed in a tubular shape, the through hole 113 may be filled with a part of a subcutaneous tissue when the probe part 111 is inserted into the skin, and may cause damage to a tissue or blood vessel. Accordingly, the probe part 111 is inserted into the skin after the stylet 124 has been coupled to the through hole 113 inside the probe part 111. The stylet 124 is coupled to the probe part 111 and inserted into the skin along with the probe part 111, and thus a grip is preferably mounted on the rear end of the stylet 124 in order to transfer force to the probe part 111 and the stylet 124.

The overall diameter of the needle 130 from one end thereof to the other end thereof is smaller than that of the through hole 113 of the probe part 111 so that the needle 130 can pass through the through hole 113 of the probe part 111 and the lifting location 141, can pierce through a subcutaneous tissue, and can exit from the skin. The length of the needle 130 is longer than that of the sheath 110, and an eye is formed at the rear end of the needle 130 so that the thread 131 without a cog and a barb is inserted into the eye.

Since the length of the needle 130 is longer than that of the sheath 110, the needle 130 pierces through a subcutaneous tissue, and exits from the skin after passing through the sheath 110. When the length of the needle 130 is shorter than that of the sheath 110, the needle 130 cannot pass through the sheath 110, cannot pierce through a subcutaneous tissue, and cannot exit from the skin. Accordingly, the length of the needle 130 is required to be sufficiently longer than that of the sheath 110.

A part of the thread 131 without a cog and a barb is inserted into the eye of the needle 130, and exits from the skin along with the needle 130 when the needle 130 passes through the through hole 113 of the probe part 111 and the lifting location 141, pierces through a subcutaneous tissue, and exits from the skin. The thread 131 without a cog and a barb passes through the sheath 110 and a subcutaneous tissue twice in the state in which the front and rear parts of the thread 131 without a cog and a barb have been individually inserted into the eye of the needle 130.

A method of using the lifting surgical instrument having a branch point will be described with reference to FIG. 6. The indicator 120 is inserted over the probe part 111, is slid along the probe part 111, and is then fastened at a predetermined location. The predetermined location is changed based on the depth to which the probe part 111 is inserted, and the depth to which the probe part 111 is inserted for a lifting surgery is variable. The introduction hole 142 through which the front end of the probe part 111 is inserted is required to be formed at the location which makes surgical scars preferably less visible and at which a surgery be easily performed. The location of the probe part 111 may be changed based on the location of a droopy subcutaneous tissue or wrinkle required to be lifted.

Furthermore, the size of the face varies from person to person, and thus the distance between the introduction hole 142 through which the probe part 111 is inserted and the lifting location 141 at which a droopy tissue is required to be lifted varies. Accordingly, the depth to which the probe part 111 is inserted varies.

Moreover, a second thread may be also inserted for a surgery after a first thread has been inserted. When the second thread is inserted for the surgery, the depth to which the probe part 111 is inserted may be changed, and the changed depth may be controlled via the indicator 120.

Figure 8A:
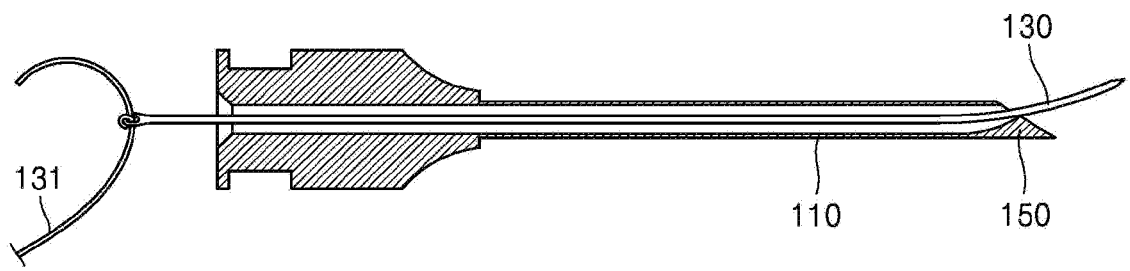
FIGS. 8a and 8b are views showing paths of a needle based on a direction guidance portion according to an embodiment of the present invention.
Figure 8B:
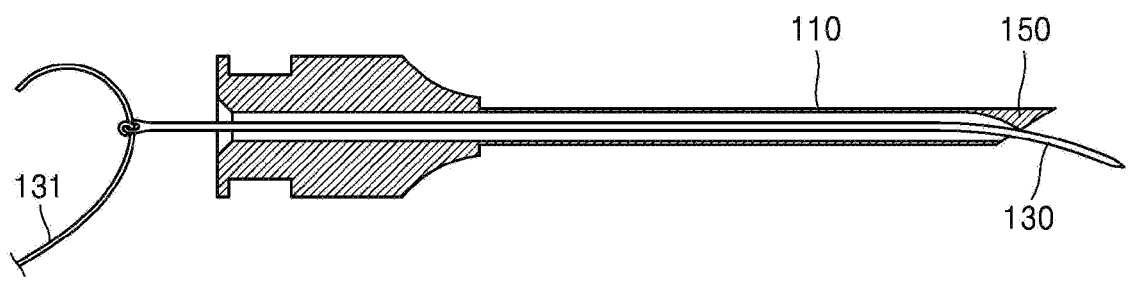

Referring to FIGS. 8a and 8b, by using the direction guidance portion 150, the path of the needle 130 traveling in a subcutaneous tissue after the front part of the thread 131 without a cog and a barb has been inserted into the needle 130 and the needle 130 has exited from the front end of the probe part 111 may be made different from the path of the needle 130 traveling in a subcutaneous tissue after the rear part of the thread 131 without a cog and a barb has been inserted into the needle 130 and the needle 130 has exited from the front end of the probe part 111. The lifting surgical instrument according to the present invention is used for a lifting surgery in which the thread 131 without a cog and a barb is formed in a ring shape under the skin, and thus the paths of the needle 130 configured to be inserted twice and travel in subcutaneous tissues are required to be made different in order to form the thread 131 without a cog and a barb in a ring shape.

In the case in which the paths of the needle 130 inserted twice, which are formed after the front end of the probe part 111, are the same as each other, a ring shape cannot be formed, and thus a tissue cannot be lifted. In the case in which the paths of the needle 130 inserted twice, which are formed after the front end of the probe part 111, partially overlap each other, the location at which the thread 131 without a cog and a barb is curved is spaced apart from the front end of the probe part 111 even when the thread 131 without a cog and a barb is formed in a ring shape. Accordingly, a surgeon cannot lift a desired tissue. The direction guidance portion 150 makes the paths of the needle 130, passing through the direction guidance portion 150 twice, different, thereby providing the effect of preventing the above-described problems from occurring (FIGS. 8a and 8b exaggeratedly illustrate the process in which the needle 130 is curved and the paths of the needle 130 are changed, and thus the actual curves of the needle 130 may be smaller than those illustrated in FIGS. 8a and 8b. Furthermore, as the needle 130 travels farther, the paths of the needle 130 having passed through the front end of the probe part 111 may be more separated from each other than the initial linear path of the needle 130.).

The lifting surgical instrument 100 according to the present invention is a lifting surgical instrument used to perform the lifting surgical method which is newly conceived by the applicant of the present invention and in which a lifting surgery is performed using the thread 131 without a cog and a barb, unlike the conventional lifting surgical methods in which a thread with cogs or barbs is caught in a subcutaneous tissue and is then pulled. More specifically, the new surgical method originally developed by the applicant of the present invention is configured to hold a subcutaneous tissue around a droopy wrinkle with the thread 131 without a cog and a barb in a ring shape and to directly pull the droopy subcutaneous tissue, thereby removing the wrinkle through lifting. Furthermore, another feature of the new surgical method resides in that the direction in which a thread is inserted is opposite to that of the conventional lifting surgical methods using a thread. In other words, in the conventional surgical methods using a thread, a thread is inserted in a downward direction, whereas, in the new surgical method, a thread is inserted in an upward direction.

The new surgical method using the lifting surgical instrument according to the present invention will be described in detail below with reference to FIGS. 9 to 13.

Referring to FIG. 9, the lifting location 141 at which a droopy tissue or wrinkle is present is determined, and the location of the introduction hole 142 into which the probe part 111 is inserted is determined such that the front end of the probe part 111 is located at the lifting location 141. The indicator 120 is inserted over the probe part 111, and is fastened to the probe part 111 at a predetermined location by considering the distance between the lifting location 141 and the location of the introduction hole 142.

Referring to FIG. 10, the probe part 111 in the state in which the stylet 124 has been coupled thereto and the indicator 120 has been fastened thereto is inserted into the skin, and then the probe part 111 is moved forward to the location at which the indicator 120 is caught by the introduction hole 142. In this case, the front end of the probe part 111 is located at the lifting location 141, and then the mounted stylet 124 is removed.

Figure 11:
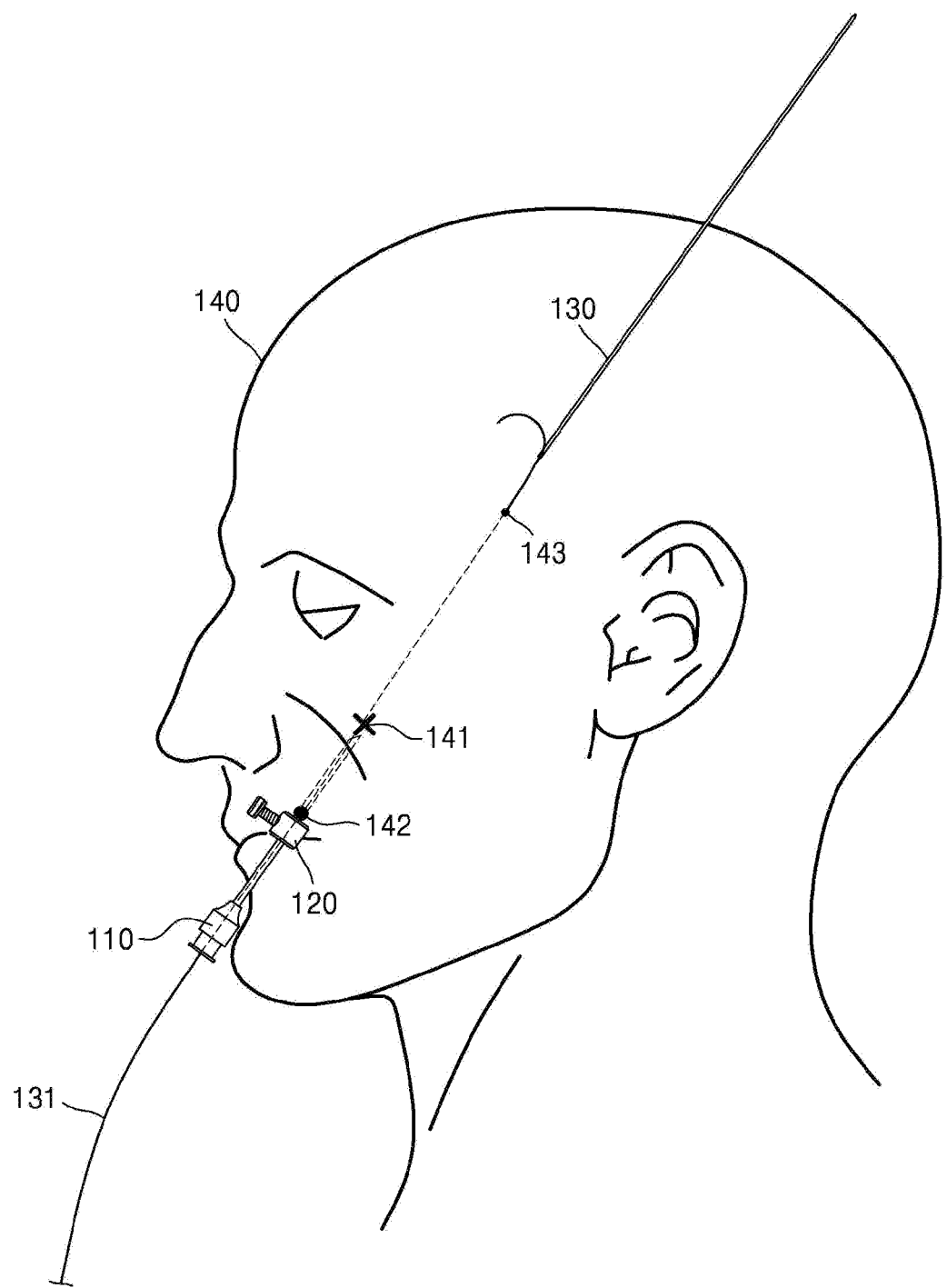

Next, referring to FIG. 11, the front part of the thread 131 without a cog and a barb is inserted into the eye of the needle 130, and the needle 130 is moved forward such that the needle 130 passes through the through hole 113 of the probe part 111 and the lifting location 141, pierces through a subcutaneous tissue, and exits from the skin through an exit 143 (in which case the exit 143 through which the needle 130 exits from the skin is preferably located in a region (mostly a scalp region) which makes surgical scars less visible).

When the needle 130 passes through the through hole 113 of the probe part 111, the direction in which the needle 130 travels is changed into a predetermined direction via the direction guidance portion 150, and the needle 130 is inserted into a subcutaneous tissue.

Figure 12:
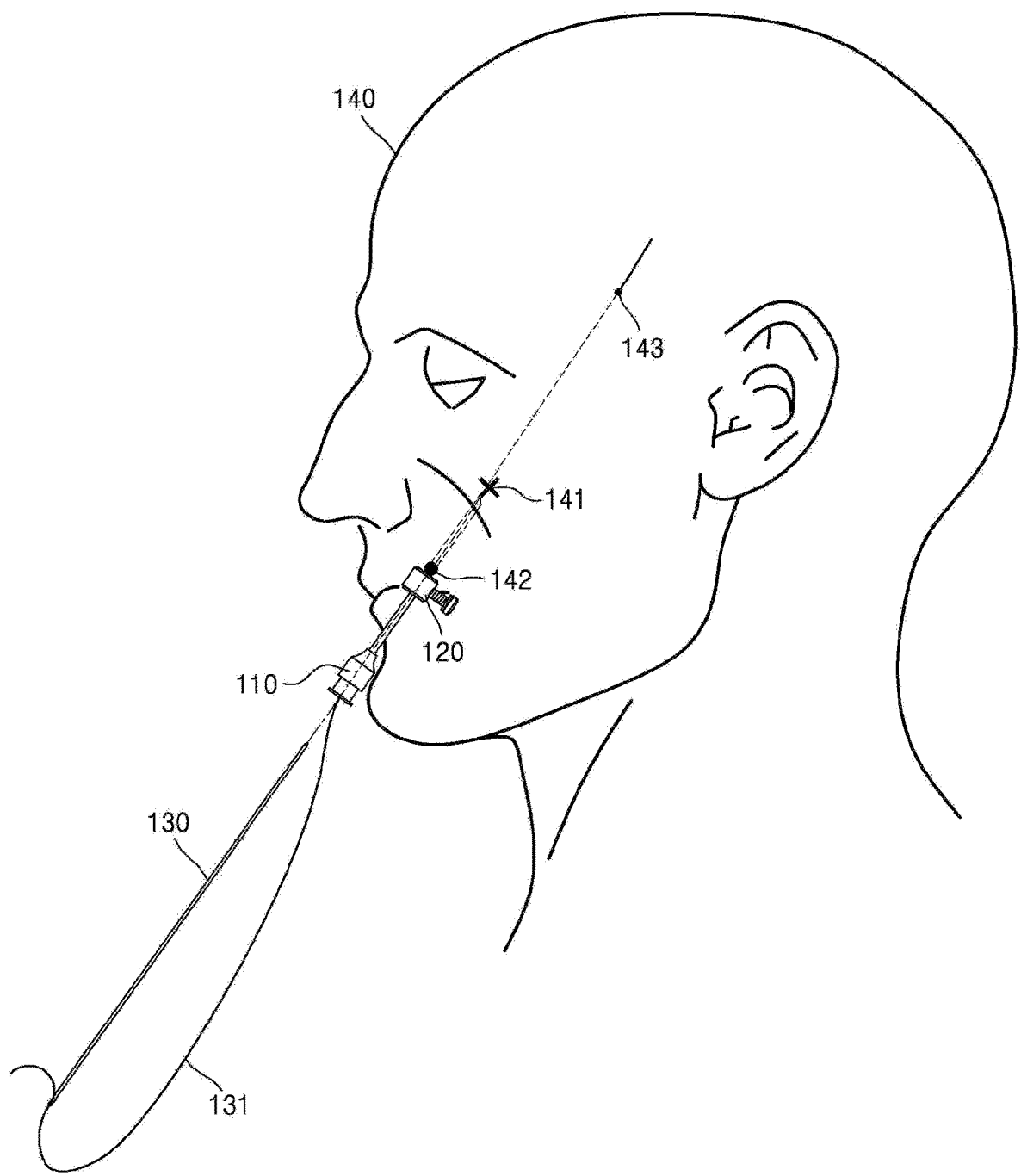

Next, referring to FIG. 12, the needle 130 is separated from the thread 131 without a cog and a barb, and the rear part of the thread 131 without a cog and a barb is inserted into the eye of the needle 130. The sheath 110 is rotated through 180 degrees, and the needle 130 is moved forward such that the needle 130 passes through the through hole 113 of the probe part 111 and the lifting location 141 once again, pierces through a subcutaneous tissue, and exits from the skin through the exit 143.

In this case, the reason why the sheath 110 is rotated through 180 degrees is to change the location of the direction guidance portion 150 and thus make the path of needle 130, into which the rear part of the thread 131 without a cog and a barb has been inserted, different from the path of needle 130 into which the front part of the thread 131 without a cog and a barb has been inserted (i.e., to make the paths of the needle 130, traveling in subcutaneous tissues after the front end of the probe part 111 through which the needle 130 has passed twice, different).

Referring to FIGS. 8a and 8b, when the sheath 110 is rotated through 180 degrees, the location of the direction guidance portion 150 disposed inside the probe part 111 is changed, and thus the path of the needle 130 is also changed. The sheath 110 is preferably rotated through 180 degrees, but the sheath 110 may be rotated through an angle other than 180 degrees if necessary.

The angle through which the sheath 110 is rotated may be checked via the bolt 122 of the indicator 120 because the bolt 122 protrudes from the indicator 120.

In other words, when the bolt 122 is screwed into the insertion hole 123 of the indicator body 121 in order to fasten the indicator 120 to the probe part 111 at a predetermined location, the location of the bolt 122 is aligned with the location of the direction guidance portion 150 of the probe part 111, and then the indicator 120 is fastened. By doing so, the location of the direction guidance portion 150 may be estimated via the bolt 122, and the path of the needle 130 may be controlled. It will be apparent that the angle through which the sheath 110 is rotated may be checked via a mark, provided on the indicator 120, or the like other than the bolt 122. For example, the angle through which the sheath 110 is rotated may be checked via the insertion hole 123 provided in the indicator 120.

Figure 13:
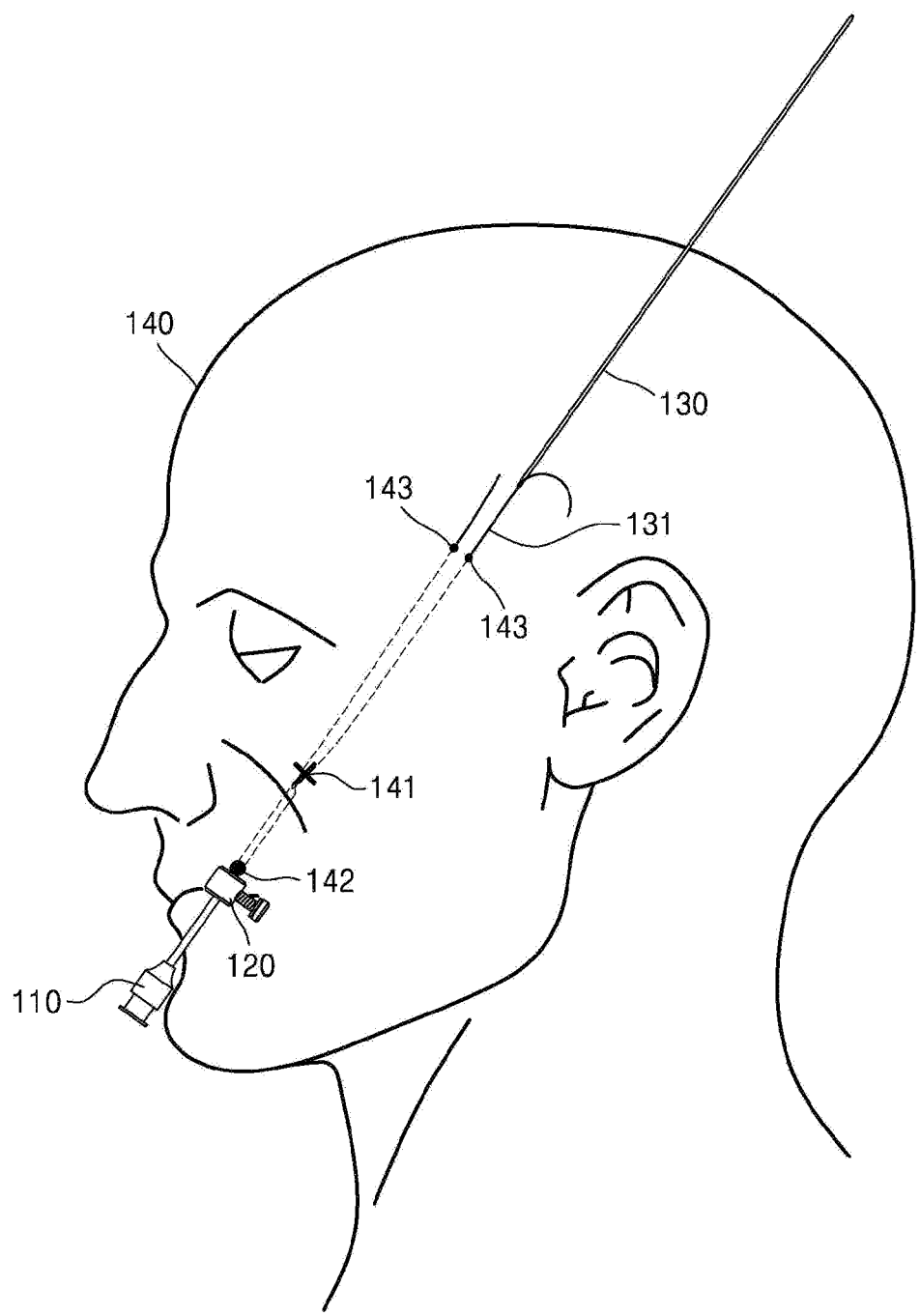

Referring to FIG. 13, a space disposed within the probe part 111 and configured to extend to the front end of the probe part 111 is empty because the probe part 111 is formed in a tubular shape, but a space disposed after the front end of the probe part 111 and configured to extend to the location at which the needle 130 exits from the skin is filled with a subcutaneous tissue. Accordingly, the part of the thread 131 without a cog and a barb, which is disposed along the path of the needle 130 which has been threaded with the front part of the thread 131 without a cog and a barb and then passed through subcutaneous tissues, and the part of the thread 131 without a cog and a barb, which is disposed along the path of the needle 130 which has been threaded with the rear part of the thread 131 and then passed through subcutaneous tissues, are independently and separately disposed within the subcutaneous tissues. Accordingly, the two parts of the thread 131 are connected to each other at the lifting location 141 within a subcutaneous tissue, and form a ring shape. In this case, the paths of the needle 130 passed through the direction guidance portion 150 twice do not overlap each other via the direction guidance portion 150, and thus the thread 131 without a cog and a barb can be easily formed in a ring shape under the skin.

Next, the opposite ends of the thread 131 without a cog and a barb having exited from the skin are pulled, and thus a subcutaneous tissue is held with the thread 131 without a cog and a barb formed in a ring shape at the lifting location 141 and then the subcutaneous tissue at the lifting location 141 is lifted or a wrinkle adjacent to the lifting location 141 is removed.

Thereafter, a surgical procedure according to the above-described surgical method may be additionally performed. In this case, the depth to which the probe part 111 is inserted may be changed by a medical doctor performing the surgical procedure, as desired. The change is made by changing the location of the indicator 120.

The effects of the indicator 120 in the new surgical method are as follows.

When a new lifting surgery in which the thread 131 without a cog and a barb is inserted and formed in a ring shape by using the needle 130 and the sheath 110 is performed, it is important that the location of the front end of the sheath 110 inserted into a subcutaneous tissue is not changed during the surgery. The reason for this is that the location of the front end of the sheath 110 is directly related to the lifting location 141 at which lifting is desired by a surgeon. Accordingly, when the location of the front end of the sheath 110 is changed, the lifting location 141 is changed, and thus the lifting location 141 is disposed at a location other than a location desired by the surgeon. For this reason, it is important that the location of the front end of the sheath 110 is not changed during the surgery.

When the needle 130 passes through the narrow, long inside of the sheath 110, frictional resistance may be generated between the needle 130 and the sheath 110. Accordingly, when the needle 130 passes through the inside of the sheath 110, the sheath 110 may be moved along with the needle 130 due to the frictional resistance, and thus the location of the front end of the sheath 110 may be changed under the skin.

Furthermore, when the needle 130 is moved forward while piercing through a subcutaneous tissue, force is applied to the needle 130. In this case, the sheath 110 may be moved along with the needle 130 due to the frictional resistance between the needle 130 and the sheath 110, and thus the location of the front end of the sheath 110 may be changed under the skin. Moreover, when the needle 130 is pulled away by pulling the needle 130 after the needle 130 has pierced through a subcutaneous tissue and has exited from the skin, frictional resistance may be generated between the needle 130 and the sheath 110, and thus the location of the front end of the sheath 110 may be changed under the skin. When the location of the front end of the sheath 110 is changed under the skin, a location other than a location desired by the surgeon becomes the lifting location 141.

When the indicator 120 according to the present invention is employed, only the part of the sheath 110 extending to the portion thereof on which the indicator 120 is disposed may be inserted into the skin. Accordingly, even when frictional resistance is generated between the needle 130 and the sheath 110, the sheath 110 does not penetrate into the skin any farther due to the indicator 120, and thus the location of the front end of the sheath 110 is not changed under the skin. Accordingly, the lifting location 141 desired by the surgeon can be prevented from being changed.

Furthermore, the needle 130 is required to pass through the sheath 110 twice in order to perform the new surgical method in which the thread 131 without a cog and a barb is inserted into the skin and is formed in a ring shape under the skin by using the needle 130 and the sheath 110, unlike in the conventional surgical methods using a thread 30 with cogs or barbs. In other words, after the needle 130 has passed through the sheath 110 for the first time and has been separated from the thread 131, the rear part of the thread 131 is required to be inserted into the eye of the needle 130 and the needle 130 is required to pass through the sheath 110 again. When the needle 130 passes through the sheath 110 a plurality of times, frictional resistance may be generated between the needle 130 and the sheath 110, and thus the location of the front end of the sheath 110 may be changed under the skin (accordingly, the lifting location 141 may be changed).

In the case in which the indicator 120 according to the present invention is employed, while the needle 130 is passing through the sheath 110 twice, the location of the front end of the sheath 110 may be checked. In this case, the indicator 120 extends the outer diameter of the sheath 110, and thus the location of the front end of the sheath 110 is not changed.

When a surgery starts, only the part of the sheath 110 extending to the portion thereof on which the indicator 120 is disposed is inserted, and thus the front end of the sheath 110 is disposed at a specific location under the skin.

In the case in which the indicator 120 is not employed, the location of the front end of the sheath 110 inserted into the skin may be changed due to frictional resistance when the long needle 130 passes through the sheath 110. However, according to the present invention, the indicator 120 is employed. Accordingly, the location of the indicator 120 is checked when the needle 130 passes through the sheath 110 for the first time, the sheath 110 is located at the location at which the indicator 120 is present before the needle 130 passes through the sheath 110 for the second time, and then the needle 130 is moved forward such that the needle 130 passes through the sheath 110 for the second time. Accordingly, the specific location, at which the front end of the sheath 110 is located when the needle 130 passes through the sheath 110 for the first time, becomes identical to the location at which the front end of the sheath 110 is located when the needle 130 passes through the sheath 110 for the second time. Therefore, even when the needle 130 passes through the sheath 110 twice, the location of the front end of the sheath 110 is not changed.

Meanwhile, there is a case in which the lifting location 141 is required to be accurately adjusted during the performance of the new lifting surgical method in which the thread 131 without a cog and a barb is inserted and formed in a ring shape by using the needle 130 and the sheath 110. In other words, even when the lifting location 141 has been determined on an external facial shape, there is a case in which the lifting location 141 is required to be accurately adjusted during the actual performance of the new lifting surgical method. Furthermore, there is a case in which the depth to which the sheath 110 is inserted may be required to be accurately and repeatedly adjusted during the performance (in other words, there is a case in which lifting is required to be performed at a plurality of lifting locations 141 rather than a single lifting location 141).

In this case, the lifting location 141 may be changed by changing the location at which the sheath 110 is inserted into the skin. When the indicator 120 is not employed, the location at which the sheath 110 has been initially inserted into the skin may not be compared with the location at which the sheath 110 is intended to be inserted into the skin. In contrast, when the indicator 120 according to the present invention is employed, the location at which the sheath 110 has been initially inserted into the skin may be determined, and thus the locations at which the sheath 110 is inserted may be accurately adjusted when the sheath 110 is repeatedly inserted. For example, when the indicator 120 is moved within a range from 2 to 3 mm, the location at which the sheath 110 is inserted is moved within a range from 2 to 3 mm, and thus the lifting location 141 may be accurately adjusted within a range from 2 to 3 mm (for this purpose, markings on the probe part 111 of the sheath 110 are preferably used). Accordingly, when the indicator 120 is employed, an advantage arises in that the new surgical method using the lifting surgical instrument according to the present invention may be more accurately performed.

The effects of the direction guidance portion 150 in the new surgical method are as follows.

In the surgical method according to the present invention in which a single ring is formed, the needle 130 passes through the through hole 113 of the probe part 111 and pierces through subcutaneous tissues twice. If the needle 130 travels along the same path or partially overlapping paths when passing through the front end of the probe part 111 and then piercing through a subcutaneous tissue or subcutaneous tissues twice, the thread 131 without a cog and a barb may not be formed in a ring shape. Even when the thread 131 is formed in a ring shape, the thread 131 starts to be curved at a location other than the location of the front end of the probe part 111, and thus a tissue may not be lifted at a location desired by a surgeon.

The direction guidance portion 150 is provided on the inner surface of the probe part 111, and thus the path of the needle 130 may be changed when the needle 130 passes through the front end of the probe part 111, thereby easily forming the thread 131 without a cog and a barb in a ring shape under the skin.

The effects of the new surgical method in which the thread 131 without a cog and a barb is formed in a ring shape and a droopy subcutaneous tissue is lifted are as follows.

First, the most conventional surgical methods using a thread are required to catch and lift a tissue by using a single strand of thread formed in a linear shape, and thus cogs or barbs are required to be formed on the surface of a thread. In the conventional surgical methods of removing a skin wrinkle by using a thread with cogs or barbs, the fastening force of cogs or barbs is weak due to the thinness of a thread, and a droopy tissue is unevenly lifted due to damage to the cogs or barbs or loss of the cogs or barbs. Furthermore, the cogs or barbs are formed on the most part of the thread, and thus the part which is not desired by a surgeon may be also influenced.

The surgical method using the surgical instrument according to the present invention is advantageous in that there is no concern about the uneven lifting of a droopy tissue because the surgical instrument does not use any cog or barb, in that sufficient fastening force may be applied by directly holding a tissue with the thread 131 at the target lifting location 141 and pulling the thread 131, and in that only a desired part may be selectively lifted.

Furthermore, in the conventional surgical methods of removing a skin wrinkle by using the thread 30 with cogs or barbs, a skin tissue may be damaged by the sharp cogs or barbs, and thus the cogs or barbs may cause a patient pain. The surgical method using the surgical instrument according to the present invention is advantageous in that a skin tissue is not damaged by cogs or barbs and a patient does not suffer from a pain attributable to cogs or barbs.

Thereafter, the probe part 111 may be located at a desired location under the skin by using the indicator 120 according to the present invention, and thus the lifting location 141 at which a subcutaneous tissue around a droopy wrinkle is intended to be lifted is prevented from being changed during a surgery, thereby being advantageous in that a lifting surgery may be performed using the thread 131 without a cog and a barb.

Additionally, when a surgery is performed using the conventional thread with cogs or barbs, a subcutaneous tissue other than a droopy subcutaneous tissue which a surgeon desires to lift may be influenced by the cogs or barbs. The lifting surgical instrument having a branch point according to the present invention holds a subcutaneous tissue with the thread 131 without a cog and a barb in a ring shape, thereby being advantageous in that only a subcutaneous tissue which a surgeon desires to lift may be selectively lifted. Furthermore, in the lifting surgical instrument having a branch point according to the present invention, the direction guidance portion 150 is provided on the probe part 111 of the sheath 110, thereby being advantageous in that the thread 131 may be easily formed in a ring shape under the skin.

The above-described lifting surgical instrument according to the present invention may be modified as follows.

Figure 14A:
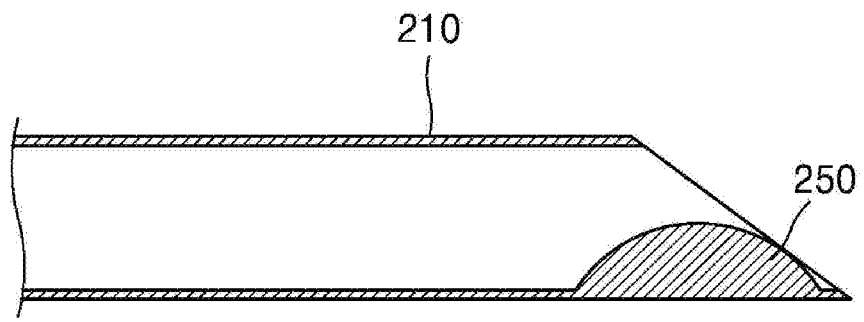
FIGS. 14a and 14b are views showing direction guidance portions according to other embodiments of the present invention.
Figure 14B:
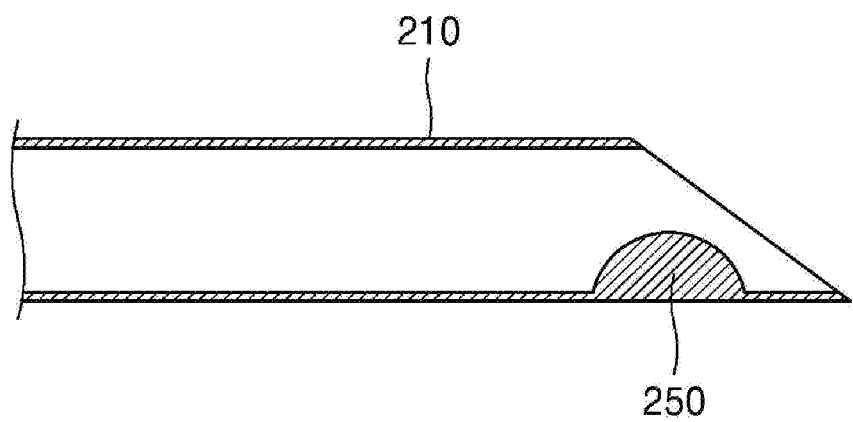

Referring to FIGS. 14a and 14b, a direction guidance portion 250 may be formed to have a semicircular sectional shape. The semicircular direction guidance portion 250 may move a needle along the front arc of the semicircular sectional shape, and the direction in which the needle travels may be easily changed via the front arc of the semicircular sectional shape. The sectional shape of the direction guidance portion 250 is not limited to the semicircular sectional shape, but the direction guidance portion 250 may be formed to have a semielliptical sectional shape. Furthermore, the semicircular direction guidance portion 250 may be provided at the front end of a probe part, but the location of the semicircular direction guidance portion 250 is not limited thereto. Referring to FIG. 14b, the semicircular direction guidance portion 250 may be provided in the middle portion of a probe part. In this case, the direction in which a needle travels is changed after the middle portion of the probe part. The direction guidance portion according to the present invention may be formed in any one of various shapes as long as these shapes enable the direction in which a needle travels to be changed.

Figure 15:
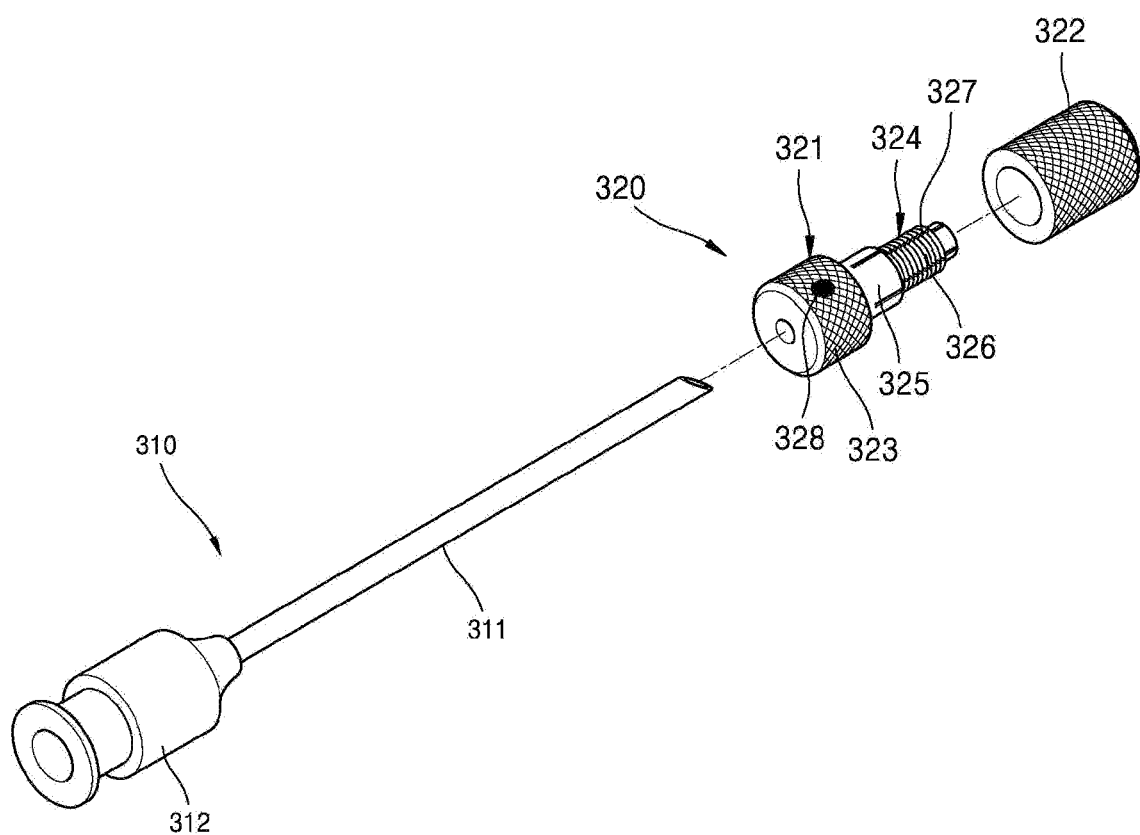
FIG. 15 is a view showing an indicator according to another embodiment of the present invention.

Referring to FIG. 15, the indicator 320 may include a body part 321 and a cover part 322 configured to be inserted over the body part 321. The body part 321 and the cover part 322 may include the respective holes into which a sheath 310 is inserted, and the indicator 320 is fastened to the sheath 310 when the cover part 322 is coupled to the body part 321.

The body part 321 includes a base part 323 formed in a cylindrical shape and a bolt part 324 configured to extend from the base part 323 and to include bolt threads 326. The bolt part 324 has a diameter smaller than that of the base part 323, and extends from the base part 323. A connection part 325 may be disposed between the base part 323 and the bolt part 324. The diameter of the connection part 325 is smaller than that of the base part 323, and is larger than that of the bolt part 324.

Screw grooves are formed in the inside of the cover part 322. The bolt part 324 of the body part 321 is screwed into the cover part 322, and the bolt threads 326 of the bolt part 324 and the screw grooves of the cover part 322 engage with each other through screw coupling. In this case, the diameter of the inside of the cover part 322 in which the screw grooves are formed is smaller than that of the bolt part 324. Since the diameter of the inside of the cover part 322 in which the screw grooves are formed is smaller than that of the bolt part 324, the cover part 322 may tighten the bolt part 324 when the bolt part 324 is completely screwed into the cover part 322.

The body part 321 and the cover part 322 may include the respective holes into which the sheath 310 is inserted, and thus the base part 323 and the bolt part 324 also include the respective holes into which the sheath 310 is inserted. In this case, the tightening of the bolt part 324 indicates that the hole of the bolt part 324 into which the sheath 310 is inserted is tightened via the screw grooves formed inside the cover part 322.

The process of fastening the above-described indicator 320 to the sheath 310 is now be described. The cover part 322 is provisionally coupled to the body part 321, and the indicator 320 is inserted over the sheath 310. The indicator 320 is disposed at the location at which the indicator 320 needs to be fastened to the sheath 310, and the cover part 322 is completely coupled to the body part 321. In a provisional coupling state, the indicator 320 may be slid along the sheath 310 because the bolt part 324 is not tightened by the screw grooves formed in the inside of the cover part 322 yet. In contrast, in a complete coupling state, the indicator 320 is not slid along the sheath 310 and fastened to the sheath 310 because the screw grooves formed in the inside of the cover part 322 tighten the bolt part 324. When the indicator 320 is required to slide along the sheath 310 again, the cover part 322 is loosened (so as to be in the provisional coupling state), and then the indicator 320 is slid.

The bolt part 324 may include grooves 327 extending in a direction perpendicular to that of the bolt threads 326. The diameter of the bolt part 324 is larger than that of the inside of the cover part 322 in which the screw grooves are formed, and thus it may be slightly difficult to insert the bolt part 324 into the cover part 322. The grooves 327 formed in the bolt part 324 provide the spaces which enable the bolt part 324 to be deformed. Accordingly, when the bolt part 324 is inserted into the cover part 322, the bolt part 324 may be partially deformed via the grooves 327, and thus the bolt part 324 may be easily inserted into the cover part 322.

A marking point 328 may be provided on the outer surface of the body part 321 or cover part 322. The direction guidance portion is provided on the probe part 311 of the sheath 310, and the location of the direction guidance portion is changed by rotating the sheath 310 so that the path of a needle is changed during a surgery. The marking point 328 is provided in order to determine the angle of the rotation of the sheath 310.

When the indicator 320 is fastened to the sheath 310, the indicator 320 is fastened in the state in which the marking point 328 provided on the indicator 320 is aligned with the direction guidance portion of the sheath 310. When the indicator 320 has been fastened to the sheath 310, the indicator 320 is rotated along with the sheath 310, and thus the angle of the rotation of the sheath 310 may be determined via the marking point 328 provided on the indicator 320.

The marking point 328 may be provided on the body part 321 or cover part 322, and may be provided on any one of various regions on the indicator 320 as long as these regions are visible to the naked eye. Furthermore, the shape of the marking point 328 may be formed in the shape of a point, but the shape of the marking point 328 is not specifically limited to the shape of a point. It will be apparent that the shape of the marking point 328 may be any one of various shapes as long as these shapes are visible to the naked eye.

The lifting surgical instrument according to the present invention has been described above with reference to various embodiments. The lifting surgical instrument according to the present invention is intended to be applied to the new surgical method in which the thread 131 without a cog and a barb is formed in a ring shape and a droopy tissue is lifted. The new surgical method and the gist of the present invention will be described below in brief.

When a single strand of thread without a cog and a barb formed in a linear shape is inserted into the skin and is pulled in order to lift a droopy tissue without an incision, the thread without a cog and a barb is not caught in a subcutaneous tissue, and thus is pulled away without lifting the droopy tissue. Accordingly, in the conventional lifting surgical methods, a single strand of thread 30 with cogs or barbs formed in a linear shape is inserted into the skin and a droopy tissue is lifted via the cogs or barbs. The conventional surgical methods are problematic in that the cogs or barbs do not provide sufficient fastening force and an undesired tissue is also lifted.

Accordingly, it is preferred that a droopy subcutaneous tissue is held and lifted using a thread without a cog and a barb. For this purpose, in the conventional surgical method, a long incision is directly made in the skin, a tissue is dissected, and a thread is directly caught in a droopy tissue under direct vision, and then the droopy tissue is lifted. The conventional surgical method is problematic in that bleeding occurs during the process of directly making the incision in the skin and surgical scars may be left.

The applicant of the present invention has conceived the new surgical method in which a droopy tissue is directly held with a thread without a cog and a barb in a ring shape without making an incision in the skin and the droopy tissue is lifted, unlike in the conventional surgical method in which a long incision is directly made in the skin and a tissue is dissected.

To perform the new surgical method, the sheath 110, the indicator 120, the needle 130, the stylet 124, and the direction guidance portion 150 provided to the sheath 110 according to the present invention are required to be used. The introduction hole 142 is formed in the skin, and the front end of the sheath 110 is located around a droopy tissue by moving the sheath 110 forward through the introduction hole 142. Thereafter, when the needle 130 is inserted twice in the state of having been threaded with the thread 131 without a cog and a barb, the thread 131 without a cog and a barb is formed in the ring shape with which the droopy tissue is held. When the thread 131 without a cog and a barb is pulled, the droopy tissue is lifted.

In the new surgical method, the sheath 110 functions as a branch point, at which the thread 131 without a cog and a barb is curved, in order to form the thread 131 without a cog and a barb in a ring shape. In particular, the direction guidance portion 150 provided to the probe part 111 makes different the paths of the needle 130, passing through the direction guidance portion 150 and traveling in subcutaneous tissues after the front end of the probe part 111 twice, thereby preventing the paths of the needle 130 from overlapping each other. Accordingly, the thread 131 without a cog and a barb, passing through the direction guidance portion 150 along with the needle 130, may be easily formed in a ring shape under the skin. Furthermore, the indicator 120 according to the present invention has been conceived in order to fasten the sheath 110 and to accurately control a depth and a distance related to the sheath 110.

Although the lifting surgical instrument according to the present invention has been described above with reference to various embodiments, the lifting surgical instrument is not limited thereto. For example, the lifting surgical instrument according to the present invention may be used to remove a droopy wrinkle of a face, and it will be apparent that the lifting surgical instrument according to the present invention may be used to lift droopy tissues of various body parts, such as a chest, a neck, a hip, and the like, or may be used to remove wrinkles in the various body parts. Furthermore, the usage of the sheath according to the present invention, to which the direction guidance portion is provided, is not limited to usage for the lifting surgical instrument, and it will be apparent that the sheath to which the direction guidance portion is provided according to the present invention may be used in the various fields in which the path of a needle is changed by changing the direction in which the needle travels.

The lifting surgical instrument having a branch point according to the present invention enables a lifting surgery to be performed by directly holding a droopy subcutaneous tissue with the thread without a cog and a barb in a ring shape, thereby being advantageous in that a decrease in fastening force attributable to damage to cogs or barbs or loss of the cogs or barbs is absent because the lifting surgical instrument does not use the method in which lifting is performed via a thread with cogs or barbs.

When a surgery is performed using the conventional thread with cogs or barbs, a tissue other than a droopy subcutaneous tissue which a surgeon desires to lift may be influenced by the cogs or barbs. The lifting surgical instrument having a branch point according to the present invention holds a subcutaneous tissue with the thread without a cog and a barb in a ring shape, thereby being advantageous in that only the tissue which a surgeon desires to lift is selectively lifted. Furthermore, in the lifting surgical instrument having a branch point according to the present invention, the direction guidance portion is provided to the probe part of the sheath, thereby being advantageous in that a ring shape may be easily formed under the skin.

Moreover, the lifting surgical instrument having a branch point according to the present invention is advantageous in that the front end of the sheath may be located at a desired location within a droopy, wrinkled skin by using the indicator and in that a wrinkle removal and lifting surgery may be performed by moving a subcutaneous tissue in an upward or desired direction via the thread without a cog and a barb.

As described above, it will be apparent that all alternatives, modifications, and equivalents which can be reasonably derived from the attached claims fall within the spirit and scope of the present invention.

What is claimed is:

1. A lifting surgical instrument comprising:
a sheath comprising a probe part formed in a tubular shape in which a through hole penetrating in a longitudinal direction is formed, the sheath having an open terminal distal end and configured such that a front end thereof can be inserted into a skin, the probe part comprising a direction guidance portion protruded from an inner surface of the probe part to the through hole, and a body configured to extend from a rear end of the probe part, to have a diameter larger than that of the through hole of the probe part, and to include a sheath hole communicating with the through hole;
a needle configured to be inserted into the sheath hole and the through hole, a length of the needle being longer than that of the sheath; and
an indicator configured to extend an outer diameter of the probe part when the indicator is inserted over an outer surface of the probe part, to slide in a longitudinal direction of the probe part, and to be fastened to the probe part at a predetermined location, thereby being caught by an introduction hole in the skin so that the probe part can be located at a desired location under the skin when the probe part is inserted into the skin,
wherein the direction guidance portion is configured such that: an angle at which the needle travels is changed via the direction guidance portion when the needle passes through the through hole of the probe part past the direction guidance portion and through the open terminal distal end of the sheath; when the direction guidance portion faces to a first direction, the needle pierces through a subcutaneous tissue and exits from the skin at a first desired location forming a first needle path; and when the body is rotated by a predetermined angle and thus the direction guidance portion faces to a second direction, the needle pierces through the subcutaneous tissue and exits from the skin at a second desired location forming a second needle path, the first needle path and the second needle path together forming a loop shape.

2. The lifting surgical instrument of claim 1, wherein the direction guidance portion is provided at the front end of the probe part.

3. The lifting surgical instrument of claim 1, wherein the direction guidance portion forms a rising curve on the inner surface of the probe part, and extends to one end of the probe part.

4. The lifting surgical instrument of claim 1, wherein:
the indicator comprises:
an indicator body configured to include an insertion hole which penetrates inner and outer surfaces thereof; and
a location fastening member configured to be inserted into the insertion hole so that the indicator can be fastened to the probe part at the predetermined location; and
screw grooves are formed in an inner surface of the insertion hole formed in the indicator body, the location fastening member includes a bolt and is screwed into the insertion hole, and the indicator is fastened to the probe part at the predetermined location when one end of the bolt inserted into the insertion hole comes in contact with an outer surface of the probe part.

5. The lifting surgical instrument of claim 1, wherein:
the indicator comprises a body part and a cover part configured to be inserted over the body part;
the body part comprises a cylindrical base part and a screw part configured to extend from the base part and to include bolt threads, and screw grooves are formed in an inner surface of the cover part;
the cover part is inserted over the screw part through a screw coupling, and a diameter of the inner surface of the cover part in which the screw grooves are formed is smaller than that of the screw part; and
the screw part is tightened when the cover part is inserted over the screw part and coupled to the screw part.

6. The lifting surgical instrument of claim 5, wherein a marking point is provided on an outer surface of the body part or cover part.

7. The lifting surgical instrument of claim 1, wherein the direction guidance portion is formed to have a semicircular or semielliptical section.

* * * * *